United States Patent
Kumar et al.

(10) Patent No.: US 9,593,086 B2
(45) Date of Patent: Mar. 14, 2017

(54) PROCESS FOR THE PREPARATION OF DEFERASIROX

(71) Applicant: Biocon Limited, Bangalore (IN)

(72) Inventors: Kothakonda Kiran Kumar, Karnataka (IN); Reddy Gearu Damodar, Andhra Pradesh (IN); Venkata Srinivas Pullela, Andhra Pradesh (IN)

(73) Assignee: Biocon Limited, Bangalore (IN)

( * ) Notice: Subject to any disclaimer, the term of this patent is extended or adjusted under 35 U.S.C. 154(b) by 0 days.

(21) Appl. No.: 14/772,728

(22) PCT Filed: Mar. 5, 2014

(86) PCT No.: PCT/IB2014/059456
§ 371 (c)(1),
(2) Date: Sep. 3, 2015

(87) PCT Pub. No.: WO2014/136062
PCT Pub. Date: Sep. 12, 2014

(65) Prior Publication Data
US 2016/0024025 A1    Jan. 28, 2016

(30) Foreign Application Priority Data
Mar. 6, 2013    (IN) .............................. 975/CHE/2013

(51) Int. Cl.
*C07D 249/08*    (2006.01)
*C07D 265/22*    (2006.01)

(52) U.S. Cl.
CPC ......... *C07D 249/08* (2013.01); *C07D 265/22* (2013.01)

(58) Field of Classification Search
None
See application file for complete search history.

(56) References Cited

FOREIGN PATENT DOCUMENTS

WO    WO2011/070560    *   6/2011

* cited by examiner

*Primary Examiner* — Samantha Shterengarts
(74) *Attorney, Agent, or Firm* — Schwegman Lundberg & Woessner, P.A.

(57) ABSTRACT

Present disclosure discloses the commercially viable process for the preparation of Deferasirox and its polymorph with. Disclosed process involves the preparation of Deferasirox via metal salt of the corresponding intermediate and deferasirox metal salt.

22 Claims, 2 Drawing Sheets

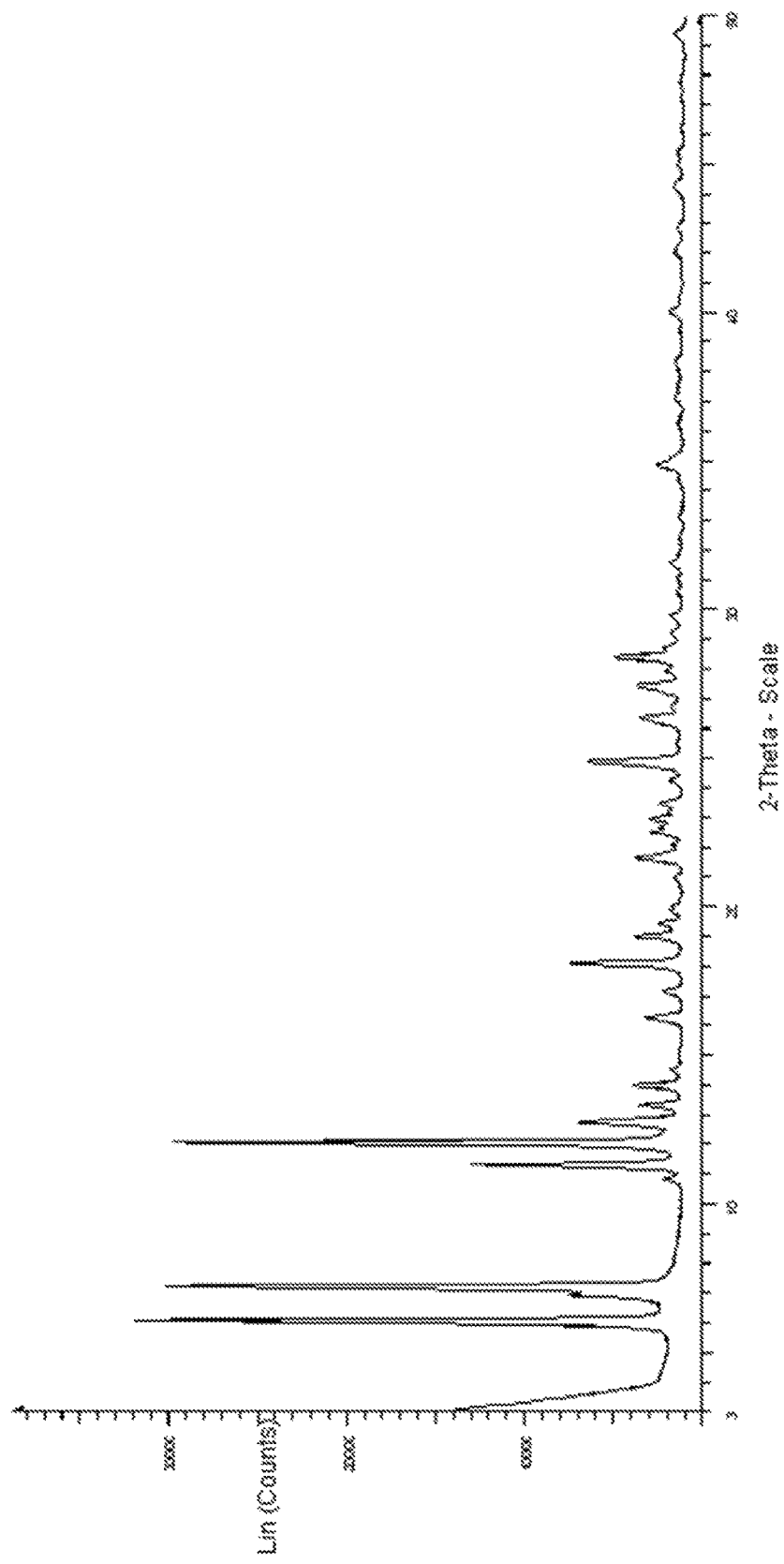
Figure 1: PXRD of 2-(2-Hydroxyphenyl)benz[e]oxazin-4-one Sodium (Sodium salt of Formula-4):

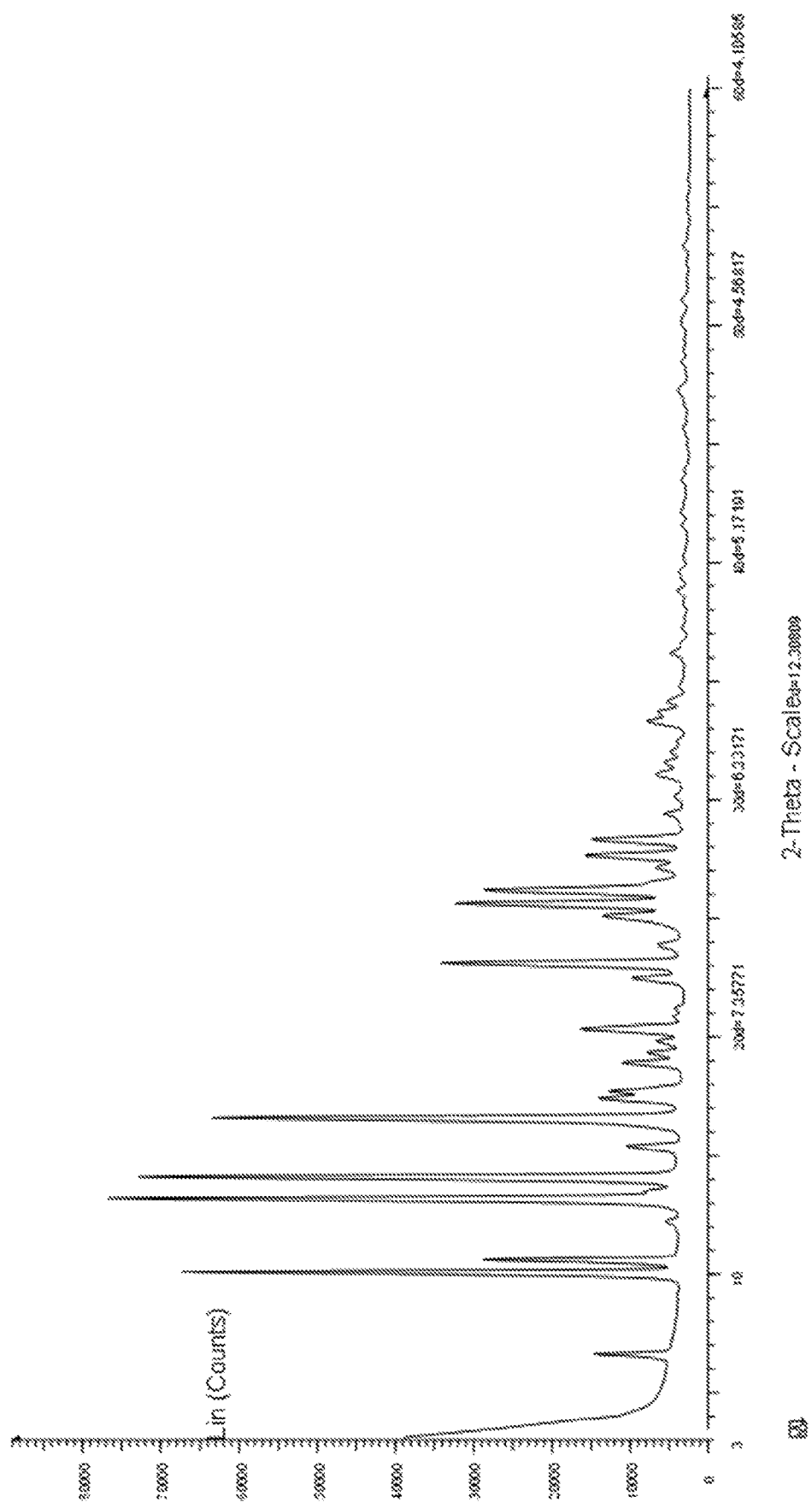
Figure 2: PXRD of Deferasirox Form-1:

PROCESS FOR THE PREPARATION OF DEFERASIROX

PRIORITY APPLICATIONS

This application is a U.S. National Stage Filing under 35 U.S.C. 371 from International Application No. PCT/IB2014/059456, filed 5 Mar. 2014, and published as WO 2014/136062 on 12 Sep. 2014, which claims the benefit under 35 U.S.C. 119 to India Application No. 975/CHE/2013, filed on 6 Mar. 2013; which applications and publication are incorporated herein by reference in their entirety.

TECHNICAL FIELD

The present disclosure discloses a robust process for the preparation of Deferasirox crystalline polymorphic form-I with superior quality. Deferasirox is prepared via novel metal salt of the corresponding intermediate and deferasirox metal salt, which enables ease of operations and ensures better quality of the product.

BACKGROUND AND PRIOR ART OF THE DISCLOSURE

Deferasirox (1) is an iron-chelator, which reduces iron overload in patients receiving long-term blood transfusions for conditions such as beta-thalassemia and other chronic anemia. It binds selectively with $Fe^{3+}$ ions in a 2:1 ratio. Deferasirox is approved by FDA and marketed as Exjade®. Chemically deferasirox is 4-[3,5-Bis (2-hydroxyphenyl)-1H-1,2,4-triazol-1yl]-benzoic acid, having molecular formula $C_{21}H_{15}N_3O_4$, and the molecular weight 373.4.

U.S. Pat. No. 6,465,504 B1 discloses substituted 3,5-diphenyl-1,2,4-triazoles and their use as pharmaceutical metal chelators in which salicyloyl chloride (Formula-2) is reacted with salicylamide (Formula-3) at 170° C. to obtain 2-(2-hydroxyphenyl)benze[e][1,3]oxazin-4-one (Formula-4) as slightly yellow crystals having melting point 206-208° C., which is then reacted with 4-hydrazinobenzoic acid (Formula-5) in ethanol under reflux conditions to obtain 4-[3,5-Bis(2-hydroxyphenyl)-1H-1,2,4-triazol-1yl]-benzoic acid (Deferasirox) as colorless crystals having melting point 264-265° C.

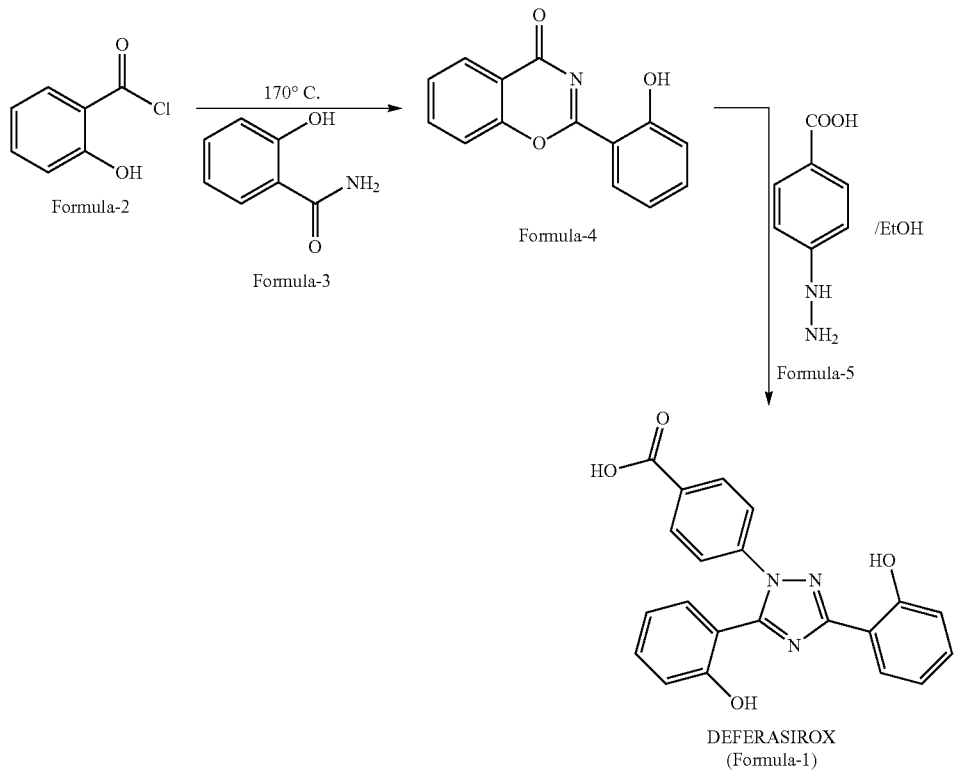

Upon the repetition of the disclosed procedure, deferasirox (1) was obtained as crystalline polymorphic form-I. However the obtained material does not meet the quality parameters such as chromatographic purity, residue on ignition, and appearance as per the ICH guidelines. Hence, a need for a more robust purification process of this crude deferasirox is inevitable to meet the quality parameters of the final API. In the reported procedures the condensation of salicyloyl chloride with salicylamide was conducted at 170° C., which is highly challenging and hazardous at commercial scales. This reaction at this combustible temperature also generates by-products such as uncyclised derivative; 2-hydroxy-N-(2-hydroxybenzoyl) benzamide compound (bis-salicylamide) of formula-6, which is difficult to remove from desired product. Though in the gram scale reactions the above said impurity is formed more than 10%, in the scale up reactions the formation of this impurity is formed about >20%. Hence, controlling the formation of this bis-salicylamide to minimum possible levels is essential.

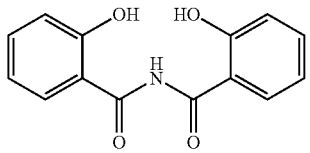

Formula-6

Crystalline polymorphic form-I of deferasirox is disclosed in IPCOM000146862D, characterized by PXRD having 2⊖ values at about 13.2, 14.1, and 16.6±0.2 degrees. The characteristic 2⊖ values of Form-I is further elaborated as 6.6, 10.0, 10.6, 20.3, 23.1, 25.7, 26.2±0.2 degrees.

WO 2008/065123 discloses use and the process of novel polymorphs designated as Form-A, B, C, D and Sb. On the other hand, WO 2008/094617 reports the polymorphic forms of deferasirox designated as Form-II, Form-III, Form-IV and their conversion to most stable polymorph Form-I. An Indian Patent application 1924/CHE/2008 reports novel solvates of deferasirox and their conversion to deferasirox.

Hence there is a great need for commercially viable process with ease of operations for the preparation of deferasirox crystalline polymorphic form-I which meets the API quality parameters and ICH limits.

STATEMENT OF THE DISCLOSURE

Accordingly, the present disclosure relates to a process for preparing crystalline form of deferasirox having purity of at least 99%, said process comprising acts of: a) reacting salicyloyl chloride of formula 2 with salicylamide of formula 3 in presence of a catalyst to obtain 2-(2-Hydroxyphenyl)benz[e]oxazin-4-one of formula 4 having less than 1% of uncyclized impurity, b) reacting salicyloyl chloride of formula 2 with salicylamide of formula 3 in presence of a catalyst and a metal base to obtain metal salt of 2-(2-Hydroxyphenyl)benz[e]oxazin-4-one of formula 4 having less than 1% of uncyclized impurity, c) reacting the 2-(2-Hydroxyphenyl)benz[e]oxazin-4-one of step (a), or the metal salt of 2-(2-Hydroxyphenyl)benz[e]oxazin-4-one of step (b), with 4-hydrozenobenzoic acid of formula 5 to obtain semi-pure form of deferasirox and d) purifying the semi-pure form of deferasirox in a solvent to obtain the crystalline form of deferasirox having purity of at least 99%; and a 2-(2-Hydroxyphenyl)benz[e]oxazin-4-one compound of formula-4 or a metal salt thereof, having less than 1% of uncyclized impurity.

BRIEF DESCRIPTION OF THE ACCOMPANYING FIGURES

In order that the disclosure may be readily understood and put into practical effect, reference will now be made to exemplary embodiments as illustrated with reference to the accompanying figures. The figures together with a detailed description below, are incorporated in and form part of the specification, and serve to further illustrate the embodiments and explain various principles and advantages, in accordance with the present disclosure wherein:

FIG. 1: shows the PXRD of 2-(2-Hydroxyphenyl)benz[e]oxazin-4-one Sodium (Sodium salt of Formula-4).

FIG. 2: shows the PXRD of Deferasirox Form-1.

DETAILED DESCRIPTION OF THE DISCLOSURE

The present disclosure relates to the process of preparation of deferasirox crystalline polymorph Form-I, which can be implemented safely in commercial scales. Surprisingly, the present disclosure addresses both process engineering aspects as well as quality aspects together. The current disclosure further refers to the reaction at reduced temperatures, controlled at formation of impurities, clarification filtration to remove the in-organic waste, and purification of the crude deferasirox to remove unwanted impurities, and color.

The present disclosure relates to a process for preparing crystalline form of deferasirox having purity of at least 99%, said process comprising acts of:
a. reacting salicyloyl chloride of formula 2 with salicylamide of formula 3 in presence of a catalyst to obtain 2-(2-Hydroxyphenyl)benz[e]oxazin-4-one of formula 4 having less than 1% of uncyclized impurity;
b. reacting salicyloyl chloride of formula 2 with salicylamide of formula 3 in presence of a catalyst and a metal base to obtain metal salt of 2-(2-Hydroxyphenyl)benz[e]oxazin-4-one of formula 4 having less than 1% of uncyclized impurity;
c. reacting the 2-(2-Hydroxyphenyl)benz[e]oxazin-4-one of step (a), or the metal salt of 2-(2-Hydroxyphenyl)benz[e]oxazin-4-one of step (b), with 4-hydrozenobenzoic acid of formula 5 to obtain semi-pure form of deferasirox; and
d. purifying the semi-pure form of deferasirox in a solvent to obtain the crystalline form of deferasirox having purity of at least 99%.

In an embodiment of the present disclosure, the catalyst is a phase transfer catalyst.

In another embodiment of the present disclosure, the phase transfer catalyst is a quaternary ammonium halide, selected from a group comprising tetra alkyl ammonium halide and benzyl tri alkyl ammonium halide or a combination thereof.

In yet another embodiment of the present disclosure, the tetra alkyl ammonium halide is selected from a group comprising tetra butyl ammonium bromide, tetra ethyl ammonium bromide, tetra butyl ammonium chloride and tetra butyl ammonium iodide or any combination thereof, and wherein the benzyl tri alkyl ammonium halide is benzyl tri alkyl ammonium bromide.

In yet another embodiment of the present disclosure, the catalyst is at an amount ranging from about is 0.001 equivalents to about 2 equivalents.

In yet another embodiment of the present disclosure, the metal base is selected from a group comprising alkali metal base and alkaline earth metal base or a combination thereof.

In yet another embodiment of the present disclosure, the metal is Lithium, Sodium, Potassium, Magnesium and Calcium or any combination thereof.

In yet another embodiment of the present disclosure, the alkali metal base or the alkaline earth metal base is selected from a group comprising Lithium Hydroxide, Sodium hydroxide, Sodium methoxide, Potassium hydroxide and Potassium tertiary butoxide, or any combination thereof.

In yet another embodiment of the present disclosure, the uncyclized impurity is 2-hydroxy-N-(2-hydroxybenzoyl) benzamide (bis-salicylamide) of formula 6.

In yet another embodiment of the present disclosure, the reaction of step (a), i.e., reacting salicyloyl chloride of formula 2 with salicylamide of formula 3 in presence of a catalyst to obtain 2-(2-Hydroxyphenyl)benz[e]oxazin-4-one of formula 4 having less than 1% of uncyclized impurity, comprises acts of:
a. adding salicylamide and the catalyst to the salicyloyl chloride in a solvent to obtain a solid mass;

b. heating the solid mass to a temperature ranging from about 90° C. to about 130° C., for a time period ranging from about 3 hours to about 5 hours, followed by cooling the mass to a temperature of less that about 40° C. followed by stirring to obtain a precipitate; and c. washing the precipitate with a solvent and drying to obtain the 2-(2-Hydroxyphenyl)benz[e]oxazin-4-one of formula 4 having less than 1% of uncyclized impurity.

In yet another embodiment of the present disclosure, the reaction of step (b), i.e., reacting salicyloyl chloride of formula 2 with salicylamide of formula 3 in presence of a catalyst and a metal base to obtain metal salt of 2-(2-Hydroxyphenyl)benz[e]oxazin-4-one of formula 4 having less than 1% of uncyclized impurity, comprises acts of:

a. adding salicylamide and the catalyst to the salicyloyl chloride in a solvent to obtain a solid mass;

b. heating the solid mass to a temperature ranging from about 90° C. to about 130° C., for a time period ranging from about 3 hours to about 5 hours, followed by cooling the mass to a temperature of less that about 40° C. followed by adding a solvent to obtain a solution;

c. filtering the solution and adding the metal base to the filtrate followed by stirring to obtain a precipitate; and d. washing the precipitate with a solvent and drying to obtain the metal salt of 2-(2-Hydroxyphenyl)benz[e]oxazin-4-one of formula 4 having less than 1% of uncyclized impurity.

In still another embodiment of the present disclosure, the reactions of step (a) and (b) of the main process as described above, are carried at temperature ranging from about 35° C. to about 170° C.

In still another embodiment of the present disclosure, the reaction of step (c), i.e., reacting the 2-(2-Hydroxyphenyl)benz[e]oxazin-4-one of step (a), or the metal salt of 2-(2-Hydroxyphenyl)benz[e]oxazin-4-one of step (b), with 4-hydrozenobenzoic acid of formula 5 to obtain semi-pure form of deferasirox, comprises acts of:

a. adding 4-hydrozenobenzoic acid to the 2-(2-Hydroxyphenyl)benz[e]oxazin-4-one of formula 4, and refluxing the reaction mixture for a time period ranging from about 1 hour to about 3 hours followed by cooling to a temperature of less that about 40° C. to obtain a precipitate; and b. washing the precipitate with a solvent and drying to obtain the semi-pure form of deferasirox In still another embodiment of the present disclosure, the reaction of step (c) of the main process comprises acts of:

a. adding 4-hydrozenobenzoic acid to the metal salt of 2-(2-Hydroxyphenyl)benz[e]oxazin-4-one of formula 4, and refluxing the reaction mixture for a time period ranging from about 1 hour to about 3 hours followed by cooling to a temperature of less that about 40° C. to obtain a precipitate; and b. washing the precipitate with a solvent to obtain a solid mass, and suspending the solid mass in the solvent followed by acidifying to a pH ranging from about 3 to about 5, to obtain a second precipitate; and c. filtering and drying the precipitate to obtain the semi-pure form of deferasirox.

In still another embodiment of the present disclosure, the acidification is carried out by acids selected from a group comprising Hydrochloric acid and Hydrobromic acid or a combination thereof.

In still another embodiment of the present disclosure, the purification of step (d), i.e., purifying the semi-pure form of deferasirox in a solvent to obtain the crystalline form of deferasirox having purity of at least 99%, comprises acts of:

a. dissolving the semi-pure form of deferasirox in a solvent at reflux temperature to obtain a reaction mass;

b. charging the reaction mass with charcoal followed by stirring for a time period ranging from about 30 minutes to about 60 minutes to obtain a solution;

c. filtering the solution followed by cooling to obtain a precipitate;

d. re-stirring the solution for a time period ranging from about 30 minutes to about 90 minutes to obtain a solid; and e. filtering and washing the solid with the solvent, followed by drying to obtain the crystalline form of deferasirox having purity of at least 99%.

In still another embodiment of the present disclosure, the purification of step (d) of the main process comprises acts of:

a. dissolving the semi-pure form of deferasirox in a solvent at reflux temperature to obtain a reaction mass;

b. charging the reaction mass with charcoal followed by stirring for a time period ranging from about 30 minutes to about 60 minutes to obtain a solution;

c. filtering the solution followed by cooling to obtain a precipitate;

d. re-stirring the solution for a time period ranging from about 30 minutes to about 90 minutes to obtain a solid; and e. filtering and washing the solid with the solvent, followed by drying to obtain the crystalline form of deferasirox having purity of at least 99%.

In still another embodiment of the present disclosure, the solvent is selected from a group comprising dichloromethane, dichloroethane, chloroform, methanol, ethanol, isopropanol, toluene, xylene, tetrahydrofuran, dimethyl formamaide, ethyl acetate, isopropyl acetate, diethyl ether, diisopropyl ether, methyl tertiary butyl ether, petroleum ether, hexanes, heptanes and water or any combination thereof.

In still another embodiment of the present disclosure, the crystalline form of deferasirox is a polymorphic form Form-I of deferasirox, having the 2$\Theta$ values 6.6, 10.0, 10.6, 20.3, 23.1, 25.7 and 26.2±0.2 degrees.

The present disclosure relates to a 2-(2-Hydroxyphenyl)benz[e]oxazin-4-one compound of formula-4 or a metal salt thereof, having less than 1% of uncyclized impurity In an embodiment of the present disclosure, the uncyclized impurity is 2-hydroxy-N-(2-hydroxybenzoyl)benzamide (bis-salicylamide) of formula 6.

In another embodiment of the present disclosure, the metal salt is a sodium salt of 2-(2-Hydroxyphenyl)benz[e]oxazin-4-one.

In still another embodiment of the present disclosure, the sodium salt of 2-(2-Hydroxyphenyl)benz[e]oxazin-4-one is characterized by PXRD, having 2$\Theta$ values at about: 6.02, 6.90, 7.18, 10.80, 11.29, 12.02, 12.73, 13.30, 13.98, 14.49, 16.29, 17.13, 18.06, 18.99, 19.42, 19.97, 20.97, 21.63, 22.50, 22.93, 23.48, 24.26, 24.89, 26.38, 26.75, 27.47, 27.95, 28.42, 29.22, 29.80, 31.57, 34.88 and 40.06±0.2 degrees.

In an embodiment of the present disclosure, salicyloyl chloride (Formula-2) is generated from salicylic acid by reacting with acid chloride selected from a group comprising thionyl chloride, oxaloyl choride, phosphoryl chloride and phosphorous pentachloride or any mixture thereof, in a suitable solvent selected from a group comprising toluene, xylene, tetrahydrofuran and dimethylformamide or any mixture thereof.

In another embodiment of the present disclosure, the resulting salicyloyl chloride (Formula-2) is reacted with salicylamide (Formula-3) in presence of a reaction stabilizer, which is a phase transfer catalyst, to obtain 2-(2-hydroxyphenyl)benze[e][1,3]oxazin-4-one (Formula-4) with maximum conversion and having minimal by-product (Formula-6) in the reaction mixture crude.

In an embodiment, the phase transfer catalyst is a quaternary ammonium halide, selected from a group comprising tetra alkyl ammonium halide and benzyl tri alkyl ammonium halide or a combination thereof. In an embodiment, the tetra alkyl ammonium halide is selected from a group comprising tetra butyl ammonium bromide, tetra ethyl ammonium bromide, tetra butyl ammonium chloride and tetra butyl ammonium iodide or any combination thereof. In a further embodiment, the benzyl tri alkyl ammonium halide is benzyl tri alkyl ammonium bromide.

In an embodiment of the present disclosure, the phase transfer catalyst is used in catalytic to stoichiometric ratios, which stabilizes the reaction and controls the formation of bis-salicylamide. The reaction is carried in a suitable solvent selected from a group comprising toluene, xylenes, THF, DMF and dichloromethane, or any mixture thereof, or optionally the reaction is carried out in neat. The temperature of the reaction is maintained between 35-170° C., more preferably between 65-130° C., and most preferably between 75-120° C. Moreover, the use of solvent in this reaction allows washing of the cake to remove the unwanted impurities. The recovery of the product of Formula-4 is much higher than the reported procedure.

In an embodiment of the present disclosure, the reaction mixture, wherein the product of Formula-4 is obtained, is allowed to precipitate, and the precipitate is isolated as a solid with better quality having the by-product of Formula-6 in a concentration of less than about <1%, more preferably <0.5%, most preferably <0.2%. Optionally, intermediate of Formula-4 is also extracted in solution form into organic solvents selected from a group comprising dichloromethane, dichloroethane and chloroform or any mixture thereof, and then carried to the next reaction.

In a further embodiment of the present disclosure, intermediate compound having Formula-4 or sodium salt of the intermediate Formula-4 is prepared in a single operation by following: to salicylic acid, salicylamide and TBAB, in dimethyl formamide/toluene mixture and thionyl chloride is added and reacted till the completion of the reaction. After the completion of the reaction, volatile compounds are distilled off from the reaction mixture. Isopropanol is added, and the solid is separated by filtration. In case of sodium salt: after the completion of the reaction, sodium methoxide is added to the reaction mixture. The resultant sodium salt is precipitated and isolated by filtration.

In a further embodiment of the present disclosure, after the completion of the reaction between salicyloyl chloride and salicylamide in presence of the Phase Transfer Catalyst, the reaction mixture is dissolved in dichloromethane and sodium methoxide was added to form the corresponding sodium salt of the intermediate 2-(2-hydroxyphenyl)benze[e][1,3]oxazin-4-one (Formula-4). The salt so formed is allowed to precipitate and the precipitate is further isolated by filtration. The salt is found to be pure and crystalline in nature. Polymorph of the sodium salt of Formula-4 is characterized by PXRD designated as Form-X, having 2Θ values at about: 6.02, 6.90, 7.18, 10.80, 11.29, 12.02, 12.73, 13.30, 13.98, 14.49, 16.29, 17.13, 18.06, 18.99, 19.42, 19.97, 20.97, 21.63, 22.50, 22.93, 23.48, 24.26, 24.89, 26.38, 26.75, 27.47, 27.95, 28.42, 29.22, 29.80, 31.57, 34.88, 40.06±0.2.

In another embodiment of the present disclosure, to produce deferasirox, 2-(2-hydroxyphenyl)benze[e][1,3]oxazin-4-one (Formula-4) or the corresponding sodium salt is reacted with 4-hydrazinobenzoic acid (Formula-5) in suitable solvent such as a C1-C4 alcohol selected from a group comprising methanol, ethanol, isopropanol, dimethylformamide, dichloromethane and water or any mixture thereof. More preferably, when C1-C4 alcohols or aqueous alcohols are used as solvents the purity and the conversions are better. Most preferably, water is used as single solvent for this reaction. The volumes of solvents used are 2-70 volumes, more preferably 10-45 volumes and most preferably 20-35 volumes. The temperature of the reaction is maintained between 35-120° C., more preferably between 50-110° C. and most preferably between 65-105° C. After the completion of the reaction, the mass is cooled to less than about 70° C., more preferably to less than 45° C. and most preferably to less than 30° C., for complete precipitation. Thereafter the precipitated solid is isolated. The isolated wet cake is optionally washed, and sucked dry. The material isolated is semi-pure with respect to the chromatographic purity having about >99% purity and the appearance is greyish pale yellow.

In a further embodiment of the present disclosure, the reaction between sodium salt of 2-(2-hydroxyphenyl)benze[e][1,3]oxazin-4-one and 4-hydrazinobenzoic acid (Formula-5) results in the sodium salt of the deferasirox. This is then suspended in organic solvent such as isopropanol and acidified with aqueous acid such as hydrochloric acid. The resulting mixture is allowed to precipitate, and the resultant deferasirox is isolated as crystalline polymorphic form-1.

In another embodiment of the present disclosure, the semi-pure deferasirox (optionally dried cake) is purified to obtain the substantially pure deferasirox colorless crystals with >99.2% chromatographic purity. The solvents used for purification are C1-C4 alcohols selected from a group comprising methanol, ethanol and isopropanol, lower chain esters selected from a group comprising ethyl acetate and isopropyl acetate, lower chain ethers selected from a group comprising diethyl ether, diisopropyl ether and methyl tertiary butyl ether, hydrocarbons selected from a group comprising petroleum ether, hexanes and heptanes, or any mixture thereof. The volumes of solvents used are between 5-75 volumes, more preferably between 10-50 volumes and most preferably between 15-45 volumes. The temperature of the purification process is between 20-120° C., more preferably between 40-90° C. and most preferably between 50-85° C. Optionally, charcoal treatment is given to remove the color impurities, and filtered through the celite to remove the insoluble particles. Addition of the solvent to the semi-pure deferasirox is done in portion wise, or on continuous basis, or in one shot at appropriate temperature. Clarified deferasirox solution is allowed to cool for precipitation, and further stirred for complete precipitation. The resulted solid is isolated by filtration, or centrifugation. Optionally, the wet-cake is washed and sucked dry under vacuum. The isolated material is further dried under vacuum at appropriate temperature till it meets the residual solvents limits as per ICH. The final deferasirox is found to be substantially pure having the chromatographic purity >99.2%, more preferably >99.5% and most preferably >99.7%. The PXRD of the isolated deferasirox is having peaks pertaining to Form-I at about 2Θ values 6.6, 10.0, 10.6, 20.3, 23.1, 25.7, 26.2±0.2 degrees.

A more complete understanding can be obtained by reference to the following specific examples, which are provided for purposes of illustration only and are not intended to limit the scope of the disclosure.

EXAMPLES

To know the product quality of Formula 4, experimental procedure disclosed in U.S. Pat. No. 6,465,504 B1 has been repeated as per: Salicylic chloride has been prepared from Salicylic acid. To salicyloyl Chloride, salicylamide is added and the reaction is heated >170° C. and then maintained for about 0.5 h. The reaction mass is cooled to 70° C., ethanol is added, and then cooled to room temperature. The suspension is filtered, the wet cake is washed with ethanol and the material is dried. (Recovery: 80%, purity: 74%, Impurity Formula-6: 16.9%).

Example-1

Preparation of Salicyloyl Chloride (Formula-2)

Thionyl chloride (0.65 L) is added slowly to salicyclic acid (1 Kg) in toluene (10 L)/DMF (100 mL) and heated to about 70-75° C. along with stirring. The stirring is continued for about 1 h and the volatile components are distilled off to obtain the syrup of salicyloyl chloride (Formula-2) (1.1 Kg).

Example-2

Preparation of Salicyloyl Chloride (Formula-2)

Oxaloyl chloride (1 L) is added slowly to salicyclic acid (1.2 Kg) in tetrahydrofuran (10 L)/DMF (100 mL) and heated to about 50-75° C. along with stirring. The stirring is continued for about 1 h and the volatile components are distilled off to obtain the syrup of salicyloyl chloride (Formula-2) (1.3 Kg).

Example-3

Typical Preparation of 2-(2-Hydroxyphenyl)benz[e]oxazin-4-one (Formula-4) Using Phase Transfer Catalyst To the salicyloyl chloride (Formula-2) (1 Kg) in toluene (10 L), salicylamide (Formula-3) (1 Kg), and phase transfer catalyst (selected from the list provided in the description) (100 g) are added and the resulting mass is heated to about 110° C. for about 4 h. Subsequently, the reaction mixture is cooled to about <40° C., and the stirring is continued till the complete precipitation. Thereafter, Isopropanol (5 L) is added to the suspension, and stirred for about 1 h to obtain and isolate the precipitated solid by filtration. The obtained solid is washed with isopropanol (1 L), and the material is dried to obtain compound of Formula-4 (1.3 Kg) containing impurity (Formula-6) of less than 0.3%.

Example-4

Preparation of 2-(2-Hydroxyphenyl)benz[e]oxazin-4-one (Formula-4)

To the salicyloyl chloride (Formula-2) (110 g) in toluene (1 L), salicylamide (Formula-3) (119 g), and tetra butyl ammonium bromide (1 g) are added and the resulting mass is heated to about 110° C. for about 4 h. Subsequently, the reaction mixture is cooled to about <40° C., and the stirring is continued till complete precipitation. Thereafter, Isopropanol (500 ml) is added to the suspension, and stirred for about 30 min to obtain and isolate the precipitated solid by filtration. The obtained solid is washed with isopropanol (100 ml), and the material is dried to obtain compound of Formula-4 (130 g) containing impurity (Formula-6) of less than 0.5%.

Example-5

Preparation of 2-(2-Hydroxyphenyl)benz[e]oxazin-4-one Sodium (Sodium Salt of Formula-4)

To the salicyloyl chloride (Formula-2) (330 g) in toluene (1.5 L), salicylamide (formula-3) (359 g), and tetra butyl ammonium bromide (3 g) are added, and the resulting mass is heated to reflux for about 4 h. Subsequently, the reaction mixture is cooled to ambient temperature, and dichloromethane (3 L) is added to extract the soluble materials into dichloromethane and the mixture is filtered through celite to remove insoluble material. Thereafter, sodium methoxide (1.1 eq) is added to the above filtrate and stirred for complete precipitation at ambient temperature under nitrogen for precipitation. The precipitated solid is isolated by filtration. The obtained solid is washed with dichloromethane (300 ml), and the material is dried to obtain greenish yellow solid (350 g) of sodium salt of Formula-4.

Example-6

Preparation of 4-[3,5-Bis(2-hydroxyphenyl)-[1,2,4]triazol-1-yl]benzoic acid (Deferasirox)

To about 100 g of 2-(2-Hydroxyphenyl)benz[e]oxazin-4-one (Formula-4) in isopropanol (1.5 L), about 70 g of 4-hydrozenobenzoic acid (Formula-5) is added and refluxed for about 2 h. After completion of the reaction, the reaction mixture is cooled to ambient temperature for complete precipitation. The precipitated solid is isolated by filtration. The obtained solid is washed with isopropanol (100 ml), and dried under vacuum to obtain semi-pure deferasirox (Formula-1) (125 g) having greyishyellow colour.

Example-7

Preparation of 4-[3,5-Bis(2-hydroxyphenyl)-[1,2,4]triazol-1-yl]benzoic acid (Deferasirox) from 2-(2-Hydroxyphenyl)benz[e]oxazin-4-one Sodium To about 100 g of 2-(2-Hydroxyphenyl)benz[e]oxazin-4-one sodium salt in isopropanol (1.5 L), about 70 g of 4-hydrozenobenzoic acid (Formula-5) is added and refluxed for about 2 h. After completion of the reaction, the reaction mixture is cooled to ambient temperature for complete precipitation. The precipitated solid is isolated by filtration. The obtained solid is washed with isopropanol (100 ml). The resulting solid is suspended in isopropanol and acidified to pH 4 using hydrochloric acid. The reaction mixture is stirred for complete precipitation, to obtain the precipitate having crude Deferasirox. The crude Deferasirox is isolated by filtration of the precipitate and drying the precipitate under vacuum to obtain semi-pure deferasirox (Formula-1) (125 g) having greyish yellow colour.

Example-8

Preparation of 4-[3,5-Bis(2-hydroxyphenyl)-[1,2,4]triazol-1-yl]benzoic acid (Deferasirox)

To about 200 g of 2-(2-Hydroxyphenyl)benz[e]oxazin-4-one (Formula-4) in water (3 L), about 150 g of 4-hydrozenobenzoic acid (Formula-5) is added and heated at 90° C. for 2 h. The suspension is cooled to ambient temperature for complete precipitation to obtain the precipitate. Thereafter, the precipitate is filtered and washed with isopropanol (250 ml) twice, and sucked dry to obtain deferasirox (Formula-1) (310 g) having pale yellow colour.

Example-9

Purification of 4-[3,5-Bis(2-hydroxyphenyl)-[1,2,4]triazol-1-yl]benzoic acid (Deferasirox)

About 150 g of semi-pure 4-[3,5-Bis(2-hydroxyphenyl)-[1,2,4]triazol-1-yl]benzoic acid (deferasirox) is dissolved in isopropanol (3 L)/ethyl acetate (1 L) at reflux temperature to obtain a reaction mass. The reaction mass is charged with about 2 g of charcoal and stirred for about 45 min under reflux. The resulting solution is filtered through celite bed, and the filtrate is cooled to ambient temperature for complete precipitation. The solution is further stirred for about 1 h to obtain a solid which is further isolated by filtration. The obtained solid is washed with isopropanol (150 ml), and the wet cake is dried until the residual solvent limits are met to obtain the substantially pure deferasirox (120 g) form-I as colour less crystalline material (Purity: 99.4%).

Example-10

Purification of 4-[3,5-Bis(2-hydroxyphenyl)-[1,2,4]triazol-1-yl]benzoic acid (Deferasirox)

About 275 g of semi-pure deferasirox having pale yellow colour, in isopropanol (2.5 L) and MTBE (50 ml) are heated to reflux, and 10 g of charcoal is added following the slow addition of isopropanol (3 L). The heating is continued for complete dissolution of deferasirox. The resulting solution is filtered through cartridge, and subsequently the solution is cooled for complete precipitation to obtain crystalline solid. The crystalline solid is subsequently isolated having substantially pure deferasirox form-I. The crystalline solid is washed with isopropanol (200 ml), and the wet-cake is sucked dried and further dried under vacuum until the residual solvent limits are met. The final material is form-I colour less crystalline nature having purity of about >99.5% (243 g).

Example-11

Purification of 4-[3,5-Bis(2-hydroxyphenyl)-[1,2,4]triazol-1-yl]benzoic acid (Deferasirox)

About 100 g of semi-pure 4-[3,5-Bis(2-hydroxyphenyl)-[1,2,4]triazol-1-yl]benzoic acid (deferasirox) is dissolved in isopropanol (3 L) at reflux temperature to obtain a reaction mass. The reaction mass is charged with about 2 g of charcoal and stirred for about 45 min under reflux. The solution is filtered through celite bed, and the solvent is distilled off to minimum volumes. Subsequently, ethyl acetate (6 vol) is added to the solution, and the solvent is re-distilled off to minimum volumes (2 vol). The suspension is cooled to ambient temperature for complete precipitation. The solution is further stirred for about 1 h to obtain a solid which is further isolated by filtration. The obtained solid is washed with isopropanol (150 ml) and the wet cake is dried until the residual solvent limits are met to obtain the substantially pure deferasirox (120 g) form-I as colour less crystalline material (Purity: 99.4%).

We claim:
1. A process for preparing crystalline form of deferasirox

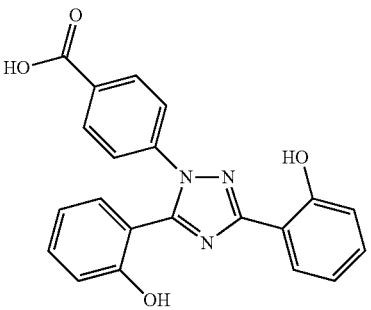

DEFERASIROX having purity of at least 99%, said process comprising acts of:
 a. reacting salicyloyl chloride of formula 2

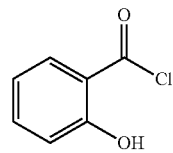

Formula-2 with salicylamide of formula 3

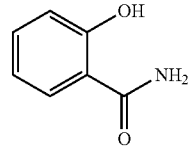

Formula-3 in presence of a catalyst to obtain 2-(2-Hydroxyphenyl)benz[e]oxazin-4-one of formula 4

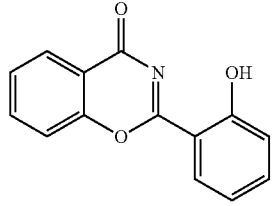

Formula-4 having less than 1% of uncyclized impurity;
 b. reacting salicyloyl chloride of formula 2 with salicylamide of formula 3 in presence of a catalyst and a metal base to obtain metal salt of 2-(2-Hydroxyphenyl)benz[e]oxazin-4-one of formula 4 having less than 1% of uncyclized impurity;

c. reacting the 2-(2-Hydroxyphenyl)benz[e]oxazin-4-one of step (a), or the metal salt of 2-(2-Hydroxyphenyl)benz[e]oxazin-4-one of step (b), with 4-hydrozenobenzoic acid of formula 5

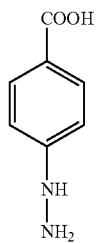

Formula-5 to obtain semi-pure form of deferasirox; and d. purifying the semi-pure form of deferasirox in a solvent to obtain the crystalline form of deferasirox having purity of at least 99%.

2. The process as claimed in claim 1, wherein the catalyst is a phase transfer catalyst.

3. The process as claimed in claim 2, wherein the phase transfer catalyst is a quaternary ammonium halide, selected from a group comprising tetra alkyl ammonium halide and benzyl tri alkyl ammonium halide or a combination thereof.

4. The process as claimed in claim 3, wherein the tetra alkyl ammonium halide is selected from a group comprising tetra butyl ammonium bromide, tetra ethyl ammonium bromide, tetra butyl ammonium chloride and tetra butyl ammonium iodide or any combination thereof; and wherein the benzyl tri alkyl ammonium halide is benzyl tri alkyl ammonium bromide.

5. The process as claimed in claim 1, wherein the catalyst is at an amount ranging from about is 0.001 equivalents to about 2 equivalents.

6. The process as claimed in claim 1, wherein the metal base is selected from a group comprising alkali metal base and alkaline earth metal base or a combination thereof.

7. The process as claimed in claim 6, wherein the metal is Lithium, Sodium, Potassium, Magnesium and Calcium or any combination thereof.

8. The process as claimed in claim 6, wherein the alkali metal base or the alkaline earth metal base is selected from a group comprising Lithium Hydroxide, Sodium hydroxide, Sodium methoxide, Potassium hydroxide and Potassium tertiary butoxide, or any combination thereof.

9. The process as claimed in claim 1, wherein the uncyclized impurity is 2-hydroxy-N-(2-hydroxybenzoyl)benzamide(bis-salicylamide) of formula 6

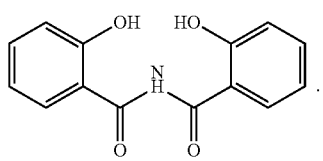

Formula-6

10. The process as claimed in claim 1, wherein the reaction of step (a) comprises acts of:

a. adding salicylamide and the catalyst to the salicyloyl chloride in a solvent to obtain a solid mass;

b. heating the solid mass to a temperature ranging from about 90° C. to about 130° C., for a time period ranging from about 3 hours to about 5 hours, followed by cooling the mass to a temperature of less that about 40° C. followed by stirring to obtain a precipitate; and c. washing the precipitate with a solvent and drying to obtain the 2-(2-Hydroxyphenyl)benz[e]oxazin-4-one of formula 4 having less than 1% of uncyclized impurity.

11. The process as claimed in claim 1, wherein the reaction of step (b) comprises acts of:

a. adding salicylamide and the catalyst to the salicyloyl chloride in a solvent to obtain a solid mass;

b. heating the solid mass to a temperature ranging from about 90° C. to about 130° C., for a time period ranging from about 3 hours to about 5 hours, followed by cooling the mass to a temperature of less that about 40° C. followed by adding a solvent to obtain a solution;

c. filtering the solution and adding the metal base to the filtrate followed by stirring to obtain a precipitate; and d. washing the precipitate with a solvent and drying to obtain the metal salt of 2-(2-Hydroxyphenyl)benz[e]oxazin-4-one of formula 4 having less than 1% of uncyclized impurity.

12. The process as claimed in claim 1, wherein the reactions of step (a) and (b) are carried at temperature ranging from about 35° C. to about 170° C.

13. The process as claimed in claim 1, wherein the reaction of step (c) comprises acts of:

a. adding 4-hydrozenobenzoic acid to the 2-(2-Hydroxyphenyl)benz[e]oxazin-4-one of formula 4, and refluxing the reaction mixture for a time period ranging from about 1 hour to about 3 hours followed by cooling to a temperature of less that about 40° C. to obtain a precipitate; and b. washing the precipitate with a solvent and drying to obtain the semi-pure form of deferasirox.

14. The process as claimed in claim 1, wherein the reaction of step (c) comprises acts of:

a. adding 4-hydrozenobenzoic acid to the metal salt of 2-(2-Hydroxyphenyl)benz[e]oxazin-4-one of formula 4, and refluxing the reaction mixture for a time period ranging from about 1 hour to about 3 hours followed by cooling to a temperature of less that about 40° C. to obtain a precipitate; and b. washing the precipitate with a solvent to obtain a solid mass, and suspending the solid mass in the solvent followed by acidifying to a pH ranging from about 3 to about 5, to obtain a second precipitate; and c. filtering and drying the precipitate to obtain the semi-pure form of deferasirox.

15. The process as claimed in claim 14, wherein the acidification is carried out by acids selected from a group comprising Hydrochloric acid and Hydrobromic acid or a combination thereof.

16. The process as claimed in claim 1, wherein the purification of step (d) comprises acts of:

a. dissolving the semi-pure form of deferasirox in a solvent at reflux temperature to obtain a reaction mass;

b. charging the reaction mass with charcoal followed by stirring for a time period ranging from about 30 minutes to about 60 minutes to obtain a solution;

c. filtering the solution followed by cooling to obtain a precipitate;

d. re-stirring the solution for a time period ranging from about 30 minutes to about 90 minutes to obtain a solid; and e. filtering and washing the solid with the solvent, followed by drying to obtain the crystalline form of deferasirox having purity of at least 99%.

17. The process as claimed in claim 1, wherein the solvent is selected from a group comprising dichloromethane, dichloroethane, chloroform, methanol, ethanol, isopropanol, toluene, xylene, tetrahydrofuran, dimethyl formamaide, ethyl acetate, isopropyl acetate, diethyl ether, diisopropyl ether, methyl tertiary butyl ether, petroleum ether, hexanes, heptanes and water or any combination thereof.

18. The process as claimed in claim 1, wherein the crystalline form of deferasirox is a polymorphic form Form-I of deferasirox, having the 2θ values 6.6, 10.0, 10.6, 20.3, 23.1, 25.7 and 26.2±0.2 degrees.

19. A 2-(2-Hydroxyphenyl)benz[e]oxazin-4-one compound of formula-4 or a metal salt thereof, having less than 1% of uncyclized impurity.

20. The compound as claimed in claim 19, wherein the uncyclized impurity is 2-hydroxy-N-(2-hydroxybenzoyl)benzamide(bis-salicylamide) of formula 6

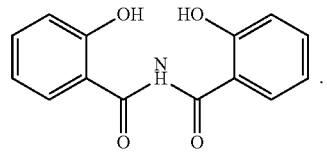

Formula-6

21. The compound as claimed in claim 19, wherein the metal salt is a sodium salt of 2-(2-Hydroxyphenyl)benz[e]oxazin-4-one.

22. The compound as claimed in claim 21, wherein the sodium salt of 2-(2-Hydroxyphenyl)benz[e]oxazin-4-one is characterized by PXRD, having 2θ values at about: 6.02, 6.90, 7.18, 10.80, 11.29, 12.02, 12.73, 13.30, 13.98, 14.49, 16.29, 17.13, 18.06, 18.99, 19.42, 19.97, 20.97, 21.63, 22.50, 22.93, 23.48, 24.26, 24.89, 26.38, 26.75, 27.47, 27.95, 28.42, 29.22, 29.80, 31.57, 34.88 and 40.06±0.2 degrees.

* * * * *